(12) United States Patent
Wang et al.

(10) Patent No.: US 12,178,754 B2
(45) Date of Patent: *Dec. 31, 2024

(54) FULL DEPTH LASER OPHTHALMIC SURGICAL SYSTEM, METHODS OF CALIBRATING THE SURGICAL SYSTEM AND TREATMENT METHODS USING THE SAME

(71) Applicant: AMO Development, LLC, Irvine, CA (US)

(72) Inventors: Jenny Wang, Mountain View, CA (US); Tianheng Wang, Fremont, CA (US); David Dewey, Sunnyvale, CA (US); Michael Wiltberger, Santa Clara, CA (US); Alexander Vankov, Mountain View, CA (US); Phillip Gooding, Mountain View, CA (US); Georg Schuele, Portola Valley, CA (US)

(73) Assignee: AMO Development, LLC, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/937,763

(22) Filed: Oct. 3, 2022

(65) Prior Publication Data

US 2023/0021864 A1 Jan. 26, 2023

Related U.S. Application Data

(60) Continuation of application No. 16/868,481, filed on May 6, 2020, now Pat. No. 11,471,328, which is a
(Continued)

(51) Int. Cl.
*A61F 9/008* (2006.01)

(52) U.S. Cl.
CPC ........ *A61F 9/0084* (2013.01); *A61F 9/00814* (2013.01); *A61F 2009/00851* (2013.01); *A61F 2009/00874* (2013.01)

(58) Field of Classification Search
CPC .... A61F 9/0084; A61F 9/00814; A61F 9/009; A61F 2009/00851; A61F 2009/00874
See application file for complete search history.

(56) References Cited

U.S. PATENT DOCUMENTS 5,459,570 A 10/1995 Swanson et al.
5,748,352 A 5/1998 Hattori
(Continued)

FOREIGN PATENT DOCUMENTS

CA 2904894 A1 10/2014

*Primary Examiner* — Carl H Layno
*Assistant Examiner* — Manolis Pahakis

(57) ABSTRACT

A full depth ophthalmic surgical system includes a femtosecond laser source and an optical coherence tomographer. The system is capable of performing surgical procedures along the entire length of the eye from the cornea to the retina. The optical system of the ophthalmic surgical system is optimized to focus the laser beam and imaging light in the vitreous humor of the eye. In some embodiments, the system includes a video camera with a tunable lens before it to image the entire length of the eye. For procedures performed posterior to the lens, a method for calibrating the full depth ophthalmic surgical system is also provided. The system can be used to perform treatment in the vitreous humor, including treating floaters and liquification of the vitreous humor.

11 Claims, 10 Drawing Sheets

Related U.S. Application Data division of application No. 16/053,724, filed on Aug. 2, 2018, now abandoned.

(56) References Cited

U.S. PATENT DOCUMENTS

| | | | |
|---|---|---|---|
| 5,748,898 A | 5/1998 | Ueda | |
| 6,053,613 A | 4/2000 | Wei et al. | |
| 6,111,645 A | 8/2000 | Tearney et al. | |
| 9,278,028 B2 | 3/2016 | Friedman et al. | |
| 10,390,996 B2* | 8/2019 | Bor | A61F 9/00831 |
| 11,471,328 B2* | 10/2022 | Wang | A61F 9/00814 |
| 2004/0054359 A1* | 3/2004 | Ruiz | A61B 3/113 606/5 |
| 2007/0219543 A1 | 9/2007 | Yee | |
| 2008/0269731 A1 | 10/2008 | Swinger et al. | |
| 2011/0118713 A1* | 5/2011 | Raksi | A61F 9/00825 606/6 |
| 2012/0140173 A1* | 6/2012 | Uhlhorn | A61B 5/7207 351/246 |
| 2012/0271286 A1 | 10/2012 | Curatu et al. | |
| 2013/0102922 A1 | 4/2013 | Gooding et al. | |
| 2013/0131652 A1* | 5/2013 | Dick | A61F 9/00802 606/4 |
| 2013/0150836 A1 | 6/2013 | Bor et al. | |
| 2014/0228825 A1 | 8/2014 | Gorschboth et al. | |
| 2014/0257257 A1 | 9/2014 | Grant et al. | |
| 2014/0276673 A1 | 9/2014 | Heitel et al. | |
| 2014/0316389 A1 | 10/2014 | Schuele et al. | |
| 2015/0031993 A1* | 1/2015 | Buckland | A61B 3/102 600/425 |
| 2015/0088103 A1 | 3/2015 | Rathjen et al. | |
| 2015/0141972 A1 | 5/2015 | Woodley et al. | |
| 2015/0342782 A1 | 12/2015 | Mordaunt et al. | |
| 2016/0074221 A1* | 3/2016 | Tassignon | G06F 16/24 606/4 |
| 2016/0074229 A1 | 3/2016 | Palanker et al. | |
| 2016/0093063 A1 | 3/2016 | Gonzalez et al. | |
| 2016/0095752 A1* | 4/2016 | Srinivasan | A61F 9/00834 606/6 |
| 2016/0183782 A1 | 6/2016 | Yu et al. | |
| 2016/0250074 A1 | 9/2016 | Fu | |
| 2016/0374857 A1 | 12/2016 | Fu et al. | |
| 2017/0326003 A1* | 11/2017 | Schuele | A61F 9/00825 |
| 2018/0303667 A1* | 10/2018 | Peyman | A61B 5/0095 |

* cited by examiner

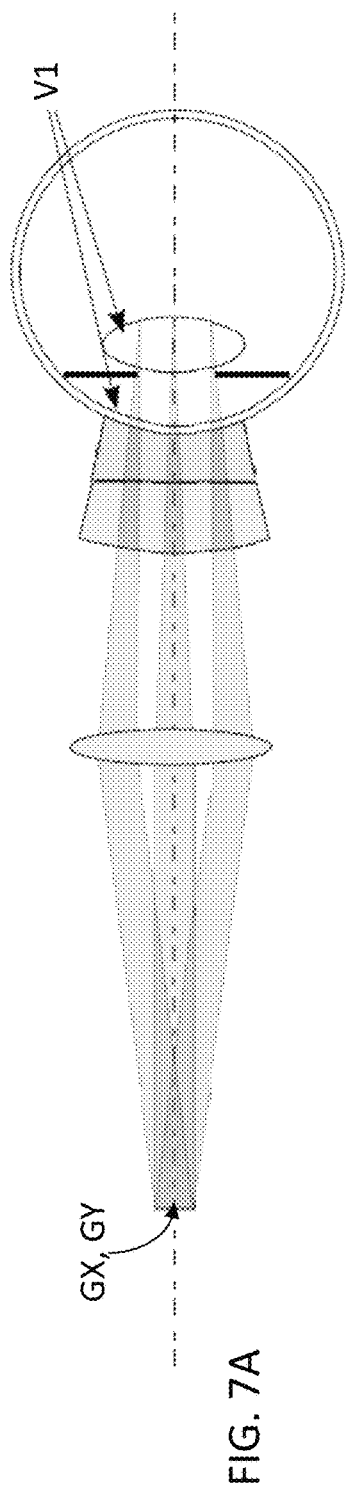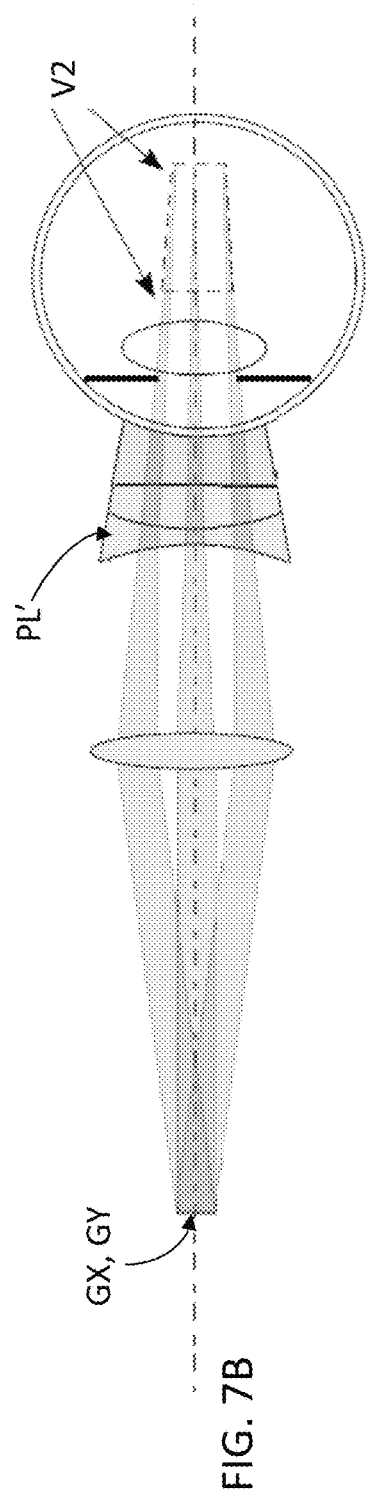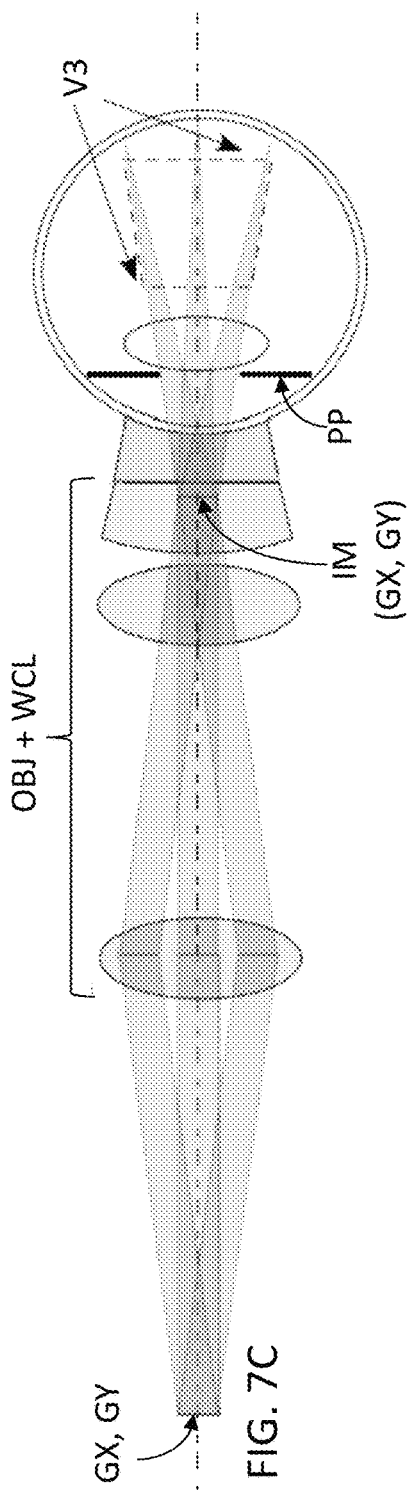

FULL DEPTH LASER OPHTHALMIC SURGICAL SYSTEM, METHODS OF CALIBRATING THE SURGICAL SYSTEM AND TREATMENT METHODS USING THE SAME

This application claims priority to and is a continuation of U.S. patent application Ser. No. 16/868,481, filed May 6, 2020, which issued as U.S. Pat. No. 11,471,328, which claims priority to and is a division of U.S. patent application Ser. No. 16/053,724, filed Aug. 2, 2018. The above-referenced applications are incorporated herein by reference in their entireties.

FIELD OF THE INVENTION

This disclosure is generally related to laser eye surgery, and more specifically to laser eye systems and methods for treating vitreous humor including ocular floaters.

BACKGROUND

Vitreous floaters are small particles consisting of cells, pigment, or fibrin that move in the vitreous of the eye. Patients with opaque vitreous humor floaters can suffer from blind spots and deteriorated vision. Vitreous surgery can improve visual acuity in these patients. Traditionally, vitreous surgery (vitrectomy) was performed by cutting the eye to remove the floaters with mechanical surgical tools, such as a vitreous infusion suction cutter that cut the vitreous and removed the debris from the eye by suction. Other vitrectomy methods have included using a nanosecond pulsed laser to tediously steer the laser visually to treat the floaters, thereby subjecting the retina to shock waves, mechanical distortions, as well as direct laser exposure of energy levels needed to treat the floaters effectively.

SUMMARY OF THE INVENTION

The techniques and systems disclosed herein provide many advantages over the current standard of care.

In one aspect, the present invention provides a full depth ophthalmic surgical system for performing surgery on eyes of subjects which includes: a femtosecond laser source configured to produce a pulsed laser beam; an imaging assembly comprising an optical coherence tomographer; a scanning assembly for deflecting the laser; a first patient interface device configured to engage an eye of a subject and configured to be removably connected to the scanning assembly, the first patient interface device having a first predefined optical power, a second patient interface device configured to engage an eye of a subject and configured to be removably connected to the scanning assembly, the second patient interface device having a second predefined optical power which is less positive or more negative than the first predefined optical power, the first patient interface and the second patient interface being alternatively connected to the scanning assembly; and a controller operably connected to the laser source, imaging assembly and scanning assembly and programmed to: operate the optical coherence tomographer to scan an imaging beam in a first eye in a first region including a lens of the first eye and structures anterior to the lens when the first patient interface is engaged with the first eye and connected to the scanning assembly, thereby obtaining image information corresponding to the first region of the first eye; operate the scanning assembly to scan a focal spot of the laser beam in the first region of the first eye to treat a tissue in the first region when the first patient interface is engaged with the first eye and connected to the scanning assembly; operate the optical coherence tomographer to scan an imaging beam in a second eye in a second region including structures posterior to a lens of the second eye when the second patient interface is engaged with the second eye and connected to the scanning assembly, thereby obtaining image information corresponding to the second region of the second eye; and operate the scanning assembly to scan a focal spot of the laser beam in the second region of the second eye to treat a tissue in the second region when the second patient interface is engaged with the second eye and connected to the scanning assembly Each of the first and the second patient interface includes: a body having an upper end and a lower end; wherein the upper end is configured to be removably attached to an objective lens assembly of the ophthalmic surgical system; a flexible suction ring disposed at the lower end of the body, configured to engage the eye via a vacuum force; and an optical assembly disposed within the body and having the respective optical power. The optical assembly is preferably a doublet lens.

In another aspect, the present invention provides a full depth ophthalmic surgical system for performing surgery on an eye of a subject, which includes: a femtosecond laser source configured to produce a femtosecond pulsed laser beam; an imaging assembly configured to emit an imaging beam; a scanning assembly including a Z scanner and an XY scanner, configured to scan a focal spot of the laser beam and the imaging beam within the eye in a depth direction and two transverse directions, respectively; an illumination light source configured to emit an illumination light; a video camera assembly; an objective lens assembly configured to focus the laser beam and the imaging beam; a patient interface configured to be coupled to the objective lens assembly and to engage the eye, the patient interface including a lens having a predefined optical power; and optical components including at least one beam splitter, configured to direct the laser beam and the imaging beam output by the scanning assembly and the illumination light to the objective lens assembly, and to direct light emitted from within the eye, which has passed through the objective lens assembly, to the video camera assembly; wherein the scanning assembly, the objective lens assembly and the lens of the patient interface are configured to form a focal spot of the laser beam at any depth within a range of 15 mm to 24 mm in water beyond a distal surface of the lens of the patient interface. The video camera assembly includes a detector and a tunable lens in front of the detector, and wherein the tunable lens of the video camera assembly is configured to focus light emitted from any distance within a range of 8 mm to 29 mm in water beyond the distal surface of the lens of the patient interface. The system further includes a fixation light source configured to generate a fixation light, wherein the optical components are further configured to direct the fixation light to the objective lens assembly. The XY scanner includes two scanning mirrors, wherein the objective lens assembly and the lens of the patient interface are configured to form respective images of the two scanning mirrors at locations 0 to 10 mm from a distal surface of the lens of the patient interface.

In another aspect, the present invention provides a method for treating a vitreous humor of an eye of a subject using a laser ophthalmic surgical system, the ophthalmic surgical system including an ultrafast laser system, an optical coherence tomographer, and shared optical components, the method including: operating the shared optical components to scan a focal zone of a light beam of the optical coherence tomographer in a region of the eye posterior to a lens of the eye; detecting an intensity of the light beam after it is reflected from the eye; determining a depth of a retina of the eye based the detected intensity of the reflected light beam; setting a first safe limiting depth which is at a predetermined distance from the depth of the retina in an anterior direction; determining another depth of another structure of the eye based the detected intensity of the reflected light beam; setting a second safe limiting depth which is at another predetermined distance from the depth of the other structure in a posterior direction; and based on the first and second safe limiting depths, operating the shared optical components to scan a focal zone of a laser beam of the ultrafast laser within a volume of the eye between the first safe limiting depth and the second safe limiting depth. The other structure of the eye may be a posterior lens capsule.

In another aspect, the present invention provides a method of liquefying the vitreous humor of the eye, which includes irradiating at least a portion of the vitreous humor of the eye with a laser beam emitted from a laser source, the laser beam comprising laser pulses having a wavelength of 1000-1100 nm, a pulse width of 100-1000 fs, a pulse energy of 2-20 µJ, a repetition rate of 1-500 kHz, and a total energy of less than 40 J.

This summary and the following detailed description are merely exemplary, illustrative, and explanatory, and are not intended to limit, but to provide further explanation of the invention as claimed. Additional aspects, features, objectives and advantages of the invention will be set forth in the descriptions that follow, and in part will become apparent from the written description, taken in conjunction with the accompanying drawings, illustrating by way of example the principles of the invention, or may be learned by practice of the invention.

BRIEF DESCRIPTION OF THE DRAWINGS

FIG. 7A schematically illustrates scanned laser beams being focused into the lens of the eye by a conventional optical beam scanning system in conjunction with a patient interface lens.

FIG. 7B schematically illustrates scanned laser beams being focused into the vitreous volume of the eye by the conventional optical beam scanning system in conjunction with another patient interface lens.

FIG. 7C schematically illustrates scanned laser beams being focused into the vitreous volume of the eye by an optical beam scanning system according to an embodiment of the present invention in conjunction with a patient interface lens.

DETAILED DESCRIPTION OF THE INVENTION

The techniques and systems disclosed herein provide many advantages over the current standard of care. Specifically, a removeable focal point extension assembly used with an existing laser ophthalmic surgical system provides a full depth ophthalmic surgical system capable of performing surgical procedures along the entire length of the eye from the cornea to the retina. A method for calibrating the full depth ophthalmic surgical system for procedures performed posterior to the lens, by using the focal zone of the optical coherence tomographer beam as a proxy for the focal zone of the femtosecond laser source, provides a fast and efficient calibration methods that can be done for each individual patient. A treatment method and system performed in the vitreous humor achieves liquification of the vitreous humor, which allows floater inclusions to move to a location where the central field of view of the eye is not affected by the floater, without disturbing other structures.

Figure 1:
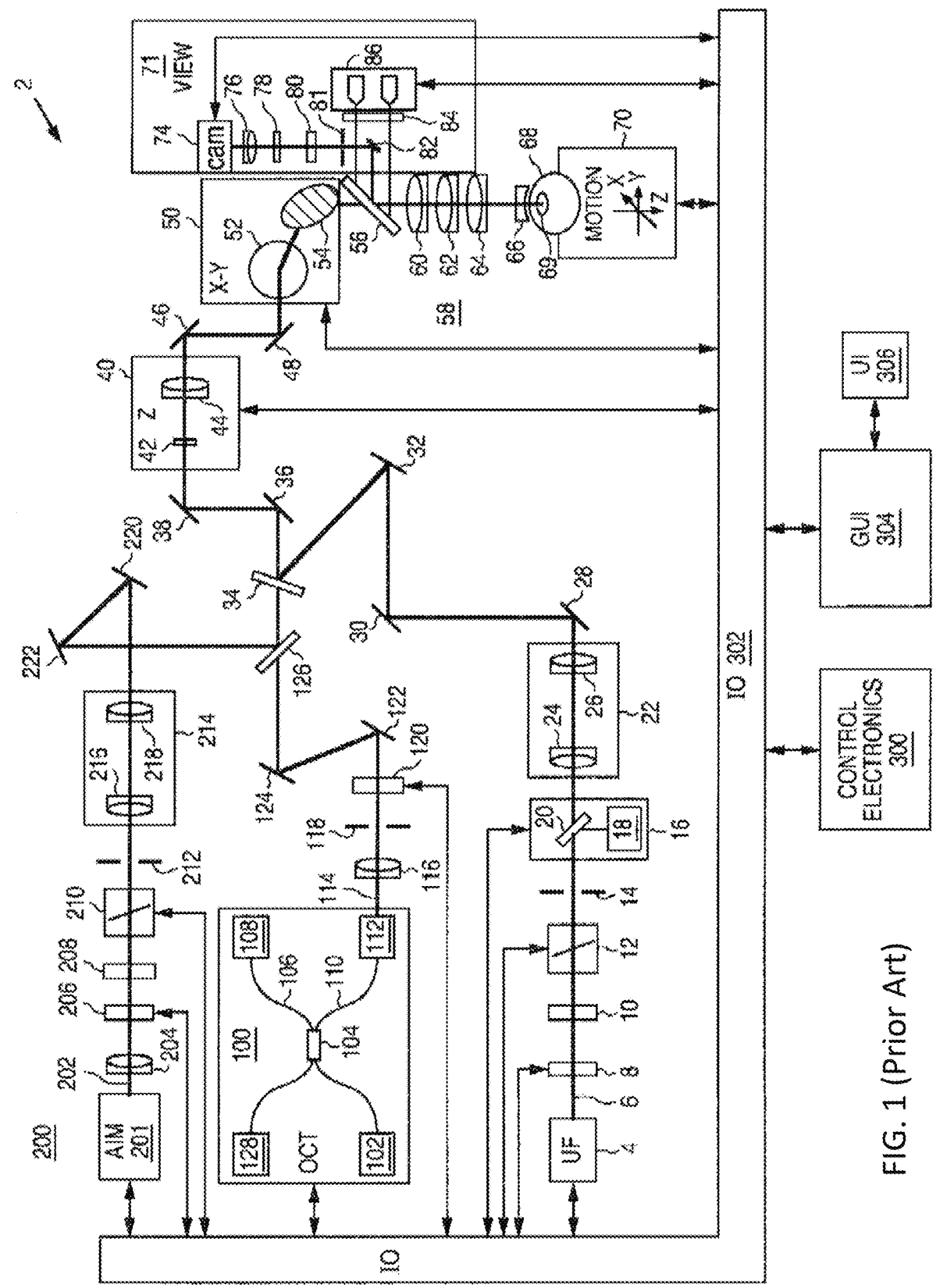
FIG. 1 is a schematic diagram of the optical beam scanning system.

The present invention can be implemented by a system that projects or scans an optical beam into a patient's eye 68, such as system 2 shown in FIG. 1 which includes an ultrafast (UF) light source 4 (e.g. a femtosecond laser, or a dual purpose system capable of emitting pulses in a lower and in a higher range of pulse energies, perhaps with different pulse durations). Using this system, a beam may be scanned in a patient's eye in three dimensions: X, Y, Z. In this embodiment, the UF wavelength can vary between 1010 nm to 1100 nm and the pulse width can vary from 100 fs to 10000 fs. The pulse repetition frequency can also vary from 10 kHz to 250 kHz. Safety limits with regard to unintended damage to non-targeted tissue bound the upper limit with regard to repetition rate and pulse energy; while threshold energy, time to complete the procedure and stability bound the lower limit for pulse energy and repetition rate. The peak power of the focused spot in the eye 68 and specifically within the crystalline lens 69 and anterior capsule of the eye is sufficient to produce optical breakdown and initiate a plasma-mediated ablation process. The peak power of the focus spot is also sufficient to treat the vitreous humor, e.g. to treat floaters or liquefy the vitreous humor, as described later. When treating the vitreous humor, the laser focus spot may be larger than when treating other parts of the eye, so the peak power will be higher to maintain sufficient peak fluence. Near-infrared wavelengths are preferred because linear optical absorption and scattering in biological tissue is reduced across that spectral range. As an example, laser 4 may be a repetitively pulsed 1035 nm device that produces 500 fs pulses at a repetition rate of 100 kHz and an individual pulse energy in the ten microjoule range. Although not illustrated, UF Light Source 4 may be further configured to provide higher energy pulses with the same or longer pulse durations than those exiting the system after pulse compression. That is, the un-compressed beam may be extracted from UF Light Source 4 in order to provide those higher energy pulses. Regardless, the following system description details means to achieve the usage of higher and/or lower energy pulses.

The laser 4 is controlled by control electronics 300, via an input and output device 302, to create optical beam 6. Control electronics 300 may be a computer, microcontroller, etc. In this example, the entire system is controlled by the controller 300, and data moved through input/output device IO 302. A graphical user interface GUI 304 may be used to set system operating parameters, process user input (UI) 306 on the GUI 304, and display gathered information such as images of ocular structures.

The generated UF light beam 6 proceeds towards the patient eye 68 passing through half-wave plate, 8, and linear polarizer, 10. The polarization state of the beam can be adjusted so that the desired amount of light passes through half-wave plate 8 and linear polarizer 10, which together act as a variable attenuator for the UF beam 6. Additionally, the orientation of linear polarizer 10 determines the incident polarization state incident upon beamcombiner 34, thereby optimizing beamcombiner throughput.

The UF beam proceeds through a shutter 12, aperture 14, and a pickoff device 16. The system controlled shutter 12 ensures on/off control of the laser for procedural and safety reasons. The aperture sets an outer useful diameter for the laser beam and the pickoff monitors the output of the useful beam. The pickoff device 16 includes of a partially reflecting mirror 20 and a detector 18. Pulse energy, average power, or a combination may be measured using detector 18. The information can be used for feedback to the half-wave plate 8 for attenuation and to verify whether the shutter 12 is open or closed. In addition, the shutter 12 may have position sensors to provide a redundant state detection.

The beam passes through a beam conditioning stage 22, in which beam parameters such as beam diameter, divergence, circularity, and astigmatism can be modified. In this illustrative example, the beam conditioning stage 22 includes a 2 element beam expanding telescope comprised of spherical optics 24 and 26 in order to achieve the intended beam size and collimation. Although not illustrated here, an anamorphic or other optical system can be used to achieve the desired beam parameters. The factors used to determine these beam parameters include the output beam parameters of the laser, the overall magnification of the system, and the desired numerical aperture (NA) at the treatment location. In addition, the optical system 22 can be used to image aperture 14 to a desired location (e.g. the center location between the 2-axis scanning device 50 described below). In this way, the amount of light that makes it through the aperture 14 is assured to make it through the scanning system. Pickoff device 16 is then a reliable measure of the usable light.

After exiting conditioning stage 22, beam 6 reflects off of fold mirrors 28, 30, & 32. These mirrors can be adjustable for alignment purposes. The beam 6 is then incident upon beam combiner 34. Beamcombiner 34 reflects the UF beam 6 (and transmits both the OCT 114 and aim 202 beams described below). For efficient beamcombiner operation, the angle of incidence is preferably kept below 45 degrees and the polarization where possible of the beams is fixed. For the UF beam 6, the orientation of linear polarizer 10 provides fixed polarization.

Following the beam combiner 34, the beam 6 continues onto the z-adjust or Z scan device 40. In this illustrative example the z-adjust includes a Galilean telescope with two lens groups 42 and 44 (each lens group includes one or more lenses). Lens group 42 moves along the z-axis about the collimation position of the telescope. In this way, the focus position of the spot in the patient's eye 68 moves along the z-axis as indicated. In general there is a fixed linear relationship between the motion of lens 42 and the motion of the focus. In this case, the z-adjust telescope has an approximate 2× beam expansion ratio and a 1:1 relationship of the movement of lens 42 to the movement of the focus. Alternatively, lens group 44 could be moved along the z-axis to actuate the z-adjust, and scan. The z-adjust is the z-scan device for treatment in the eye 68. It can be controlled automatically and dynamically by the system and selected to be independent or to interplay with the X-Y scan device described next. Mirrors 36 and 38 can be used for aligning the optical axis with the axis of z-adjust device 40.

After passing through the z-adjust device 40, the beam 6 is directed to the x-y scan device by mirrors 46 & 48. Mirrors 46 & 48 can be adjustable for alignment purposes. X-Y scanning is achieved by the scanning device 50 preferably using two mirrors 52 & 54 under the control of control electronics 300, which rotate in orthogonal directions using motors, galvanometers, or any other well known optic moving device. Mirrors 52 & 54 are located near the telecentric position of the objective lens 58 and contact lens 66 combination described below. Tilting these mirrors 52/54 causes them to deflect beam 6, causing lateral displacements in the plane of UF focus located in the patient's eye 68. Objective lens 58 may be a complex multi-element lens element, as shown, and represented by lenses 60, 62, and 64. The complexity of the lens 58 will be dictated by the scan field size, the focused spot size, the available working distance on both the proximal and distal sides of objective 58, as well as the amount of aberration control. An f-theta lens 58 of focal length 60 mm generating a spot size of 10 over a field of 10 mm, with an input beam size of 15 mm diameter is an example. Alternatively, X-Y scanning by scanner 50 may be achieved by using one or more moveable optical elements (e.g. lenses, gratings) which also may be controlled by control electronics 300, via input and output device 302.

The aiming and treatment scan patterns can be automatically generated by the scanner 50 under the control of controller 300. Such patterns may be comprised of a single spot of light, multiple spots of light, a continuous pattern of light, multiple continuous patterns of light, and/or any combination of these. In addition, the aiming pattern (using aim beam 202 described below) need not be identical to the treatment pattern (using light beam 6), but preferably at least defines its boundaries in order to assure that the treatment light is delivered only within the desired target area for patient safety. This may be done, for example, by having the aiming pattern provide an outline of the intended treatment pattern. This way the spatial extent of the treatment pattern may be made known to the user, if not the exact locations of the individual spots themselves, and the scanning thus optimized for speed, efficiency and accuracy. The aiming pattern may also be made to be perceived as blinking in order to further enhance its visibility to the user.

An optional contact lens 66, which can be any suitable ophthalmic lens, can be used to help further focus the optical beam 6 into the patient's eye 68 while helping to stabilize eye position. The positioning and character of optical beam 6 and/or the scan pattern the beam 6 forms on the eye 68 may be further controlled by use of an input device such as a joystick, or any other appropriate user input device (e.g. GUI 304) to position the patient and/or the optical system.

The UF laser 4 and controller 300 can be set to target the surfaces of the targeted structures in the eye 68 and ensure that the beam 6 will be focused where appropriate and not unintentionally damage non-targeted tissue. Imaging modalities and techniques described herein, such as for example, Optical Coherence Tomography (OCT), Purkinje imaging, Scheimpflug imaging, or ultrasound may be used to determine the location and measure the thickness of the lens and lens capsule to provide greater precision to the laser focusing methods, including 2D and 3D patterning. Laser focusing may also be accomplished using one or more methods including direct observation of an aiming beam, Optical Coherence Tomography (OCT), Purkinje imaging, Scheimpflug imaging, ultrasound, or other known ophthalmic or medical imaging modalities and/or combinations thereof. In the embodiment of FIG. 1, an OCT device 100 is described, although other modalities are within the scope of the present invention. An OCT scan of the eye will provide information about the axial location of the anterior and posterior lens capsule, the boundaries of the cataract nucleus, as well as the depth of the anterior chamber. This information is then loaded into the control electronics 300, and used to program and control the subsequent laser-assisted surgical procedure. The information may also be used to determine a wide variety of parameters related to the procedure such as, for example, the upper and lower axial limits of the focal planes used for cutting the lens capsule and segmentation of the lens cortex and nucleus, and the thickness of the lens capsule among others.

The OCT device 100 in FIG. 1 includes a broadband or a swept light source 102 that is split by a fiber coupler 104 into a reference arm 106 and a sample arm 110. The reference arm 106 includes a module 108 containing a reference reflection along with suitable dispersion and path length compensation. The sample arm 110 of the OCT device 100 has an output connector 112 that serves as an interface to the rest of the UF laser system. The return signals from both the reference and sample arms 106, 110 are then directed by coupler 104 to a detection device 128, which employs either time domain, frequency or single point detection techniques. In FIG. 1, a frequency domain technique is used with an OCT wavelength of 920 nm and bandwidth of 100 nm.

Exiting connector 112, the OCT beam 114 is collimated using lens 116. The size of the collimated beam 114 is determined by the focal length of lens 116. The size of the beam 114 is dictated by the desired NA at the focus in the eye and the magnification of the beam train leading to the eye 68. Generally, OCT beam 114 does not require as high an NA as the UF beam 6 in the focal plane and therefore the OCT beam 114 is smaller in diameter than the UF beam 6 at the beamcombiner 34 location. Following collimating lens 116 is aperture 118 which further modifies the resultant NA of the OCT beam 114 at the eye. The diameter of aperture 118 is chosen to optimize OCT light incident on the target tissue and the strength of the return signal. Polarization control element 120, which may be active or dynamic, is used to compensate for polarization state changes which may be induced by individual differences in corneal birefringence, for example. Mirrors 122 & 124 are then used to direct the OCT beam 114 towards beamcombiners 126 & 34. Mirrors 122 & 124 may be adjustable for alignment purposes and in particular for overlaying of OCT beam 114 to UF beam 6 subsequent to beamcombiner 34. Similarly, beamcombiner 126 is used to combine the OCT beam 114 with the aim beam 202 described below.

Once combined with the UF beam 6 subsequent to beamcombiner 34, OCT beam 114 follows the same path as UF beam 6 through the rest of the system. In this way, OCT beam 114 is indicative of the location of UF beam 6. OCT beam 114 passes through the z-scan 40 and x-y scan 50 devices then the objective lens 58, contact lens 66 and on into the eye 68. Reflections and scatter off of structures within the eye provide return beams that retrace back through the optical system, into connector 112, through coupler 104, and to OCT detector 128. These return back reflections provide the OCT signals that are in turn interpreted by the system as to the location in X, Y Z of UF beam 6 focal location.

OCT device 100 works on the principle of measuring differences in optical path length between its reference and sample arms. Therefore, passing the OCT through z-adjust 40 does not extend the z-range of OCT system 100 because the optical path length does not change as a function of movement of 42. OCT system 100 has an inherent z-range that is related to the detection scheme, and in the case of frequency domain detection it is specifically related to the spectrometer and the location of the reference arm 106. In the case of OCT system 100 used in FIG. 1, the z-range is approximately 1-2 mm in an aqueous environment. Extending this range to at least 4 mm involves the adjustment of the path length of the reference arm within OCT system 100. Passing the OCT beam 114 in the sample arm through the z-scan of z-adjust 40 allows for optimization of the OCT signal strength. This is accomplished by focusing the OCT beam 114 onto the targeted structure while accommodating the extended optical path length by commensurately increasing the path within the reference arm 106 of OCT system 100.

Because of the fundamental differences in the OCT measurement with respect to the UF focus device due to influences such as immersion index, refraction, and aberration, both chromatic and monochromatic, care must be taken in analyzing the OCT signal with respect to the UF beam focal location. A calibration or registration procedure as a function of X, Y Z should be conducted in order to match the OCT signal information to the UF focus location and also to the relate to absolute dimensional quantities.

Observation of an aim beam may also be used to assist the user to directing the UF laser focus. Additionally, an aim beam visible to the unaided eye in lieu of the infrared OCT and UF beams can be helpful with alignment provided the aim beam accurately represents the infrared beam parameters. An aim subsystem 200 is employed in the configuration shown in FIG. 1. The aim beam 202 is generated by an aim beam light source 201, such as a helium-neon laser operating at a wavelength of 633 nm. Alternatively a laser diode in the 630-650 nm range could be used. The advantage of using the helium neon 633 nm beam is its long coherence length, which would enable the use of the aim path as a laser unequal path interferometer (LUPI) to measure the optical quality of the beam train, for example.

Once the aim beam light source generates aim beam 202, the aim beam 202 is collimated using lens 204. The size of the collimated beam is determined by the focal length of lens 204. The size of the aim beam 202 is dictated by the desired NA at the focus in the eye and the magnification of the beam train leading to the eye 68. Generally, aim beam 202 should have close to the same NA as UF beam 6 in the focal plane and therefore aim beam 202 is of similar diameter to the UF beam at the beamcombiner 34 location. Because the aim beam is meant to stand-in for the UF beam 6 during system alignment to the target tissue of the eye, much of the aim path mimics the UF path as described previously. The aim beam 202 proceeds through a half-wave plate 206 and linear polarizer 208. The polarization state of the aim beam 202 can be adjusted so that the desired amount of light passes through polarizer 208. Elements 206 & 208 therefore act as a variable attenuator for the aim beam 202. Additionally, the orientation of polarizer 208 determines the incident polarization state incident upon beamcombiners 126 and 34, thereby fixing the polarization state and allowing for optimization of the beamcombiners' throughput. Of course, if a semiconductor laser is used as aim beam light source 200, the drive current can be varied to adjust the optical power.

The aim beam 202 proceeds through a shutter 210 and aperture 212. The system controlled shutter 210 provides on/off control of the aim beam 202. The aperture 212 sets an outer useful diameter for the aim beam 202 and can be adjusted appropriately. A calibration procedure measuring the output of the aim beam 202 at the eye can be used to set the attenuation of aim beam 202 via control of polarizer 206.

A device for imaging the target tissue on or within the eye 68 is shown schematically in FIG. 1 as imaging system 71. Imaging system includes a camera 74 and an illumination light source 86 for creating an image of the target tissue. The imaging system 71 gathers images which may be used by the system controller 300 for providing pattern centering about or within a predefined structure. The illumination light source 86 for the viewing is generally broadband and incoherent. For example, light source 86 can include multiple LEDs as shown. The wavelength of the viewing light source 86 is preferably in the range of 700 nm to 750 nm, but can be anything that is accommodated by the beamcombiner 56, which combines the viewing light with the beam path for UF beam 6 and aim beam 202 (beamcombiner 56 reflects the viewing wavelengths while transmitting the OCT and UF wavelengths). The beamcombiner 56 may partially transmit the aim wavelength so that the aim beam 202 can be visible to the viewing camera 74. Optional polarization element 84 in front of light source 86 can be a linear polarizer, a quarter wave plate, a half-wave plate or any combination, and is used to optimize signal. A false color image as generated by the near infrared wavelength is acceptable.

The illumination light from light source 86 is directed down towards the eye using the same objective lens 58 and contact lens 66 as the UF and aim beam 6, 202. The light reflected and scattered off of various structures in the eye 68 are collected by the same lenses 58 & 66 and directed back towards beamcombiner 56. There, the return light is directed back into the viewing path via beam combiner and mirror 82, and on to camera 74. Camera 74 can be, for example but not limited to, any silicon based detector array of the appropriately sized format. Video lens 76 forms an image onto the camera's detector array while optical elements 80 & 78 provide polarization control and wavelength filtering respectively. Aperture or iris 81 provides control of imaging NA and therefore depth of focus and depth of field. A small aperture provides the advantage of large depth of field which aids in the patient docking procedure. Alternatively, the illumination and camera paths can be switched. Furthermore, aim light source 200 can be made to emit in the infrared which would not directly visible, but could be captured and displayed using imaging system 71.

Coarse adjust registration is usually needed so that when the contact lens 66 comes into contact with the cornea, the targeted structures are in the capture range of the X, Y scan of the system. Therefore a docking procedure is preferred, which preferably takes in account patient motion as the system approaches the contact condition (i.e. contact between the patient's eye 68 and the contact lens 66. The viewing system 71 is configured so that the depth of focus is large enough such that the patient's eye 68 and other salient features may be seen before the contact lens 66 makes contact with eye 68.

Figure 2:
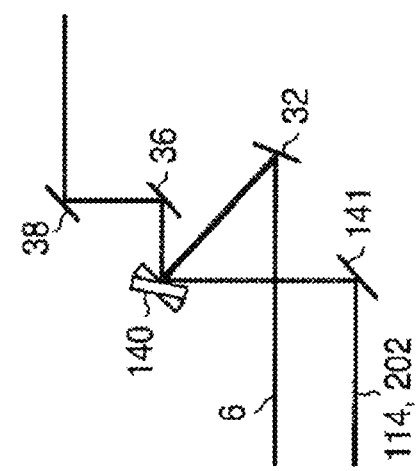
FIG. 2 is an optical diagram showing an alternative beam combining scheme.

An alternative beamcombining configuration is shown in the alternate embodiment of FIG. 2. For example, the passive beamcombiner 34 in FIG. 1 can be replaced with an active combiner 140 in FIG. 2. The active beamcombiner 34 can be a moving or dynamically controlled element such as a galvanometric scanning mirror, as shown. Active combiner 140 changes it angular orientation in order to direct either the UF beam 6 or the combined aim and OCT beams 202, 114 towards the scanner 50 and eventually eye 68 one at a time. The advantage of the active combining technique is that it avoids the difficulty of combining beams with similar wavelength ranges or polarization states using a passive beam combiner. This ability is traded off against the ability to have simultaneous beams in time and potentially less accuracy and precision due to positional tolerances of active beam combiner 140.

Figure 3:
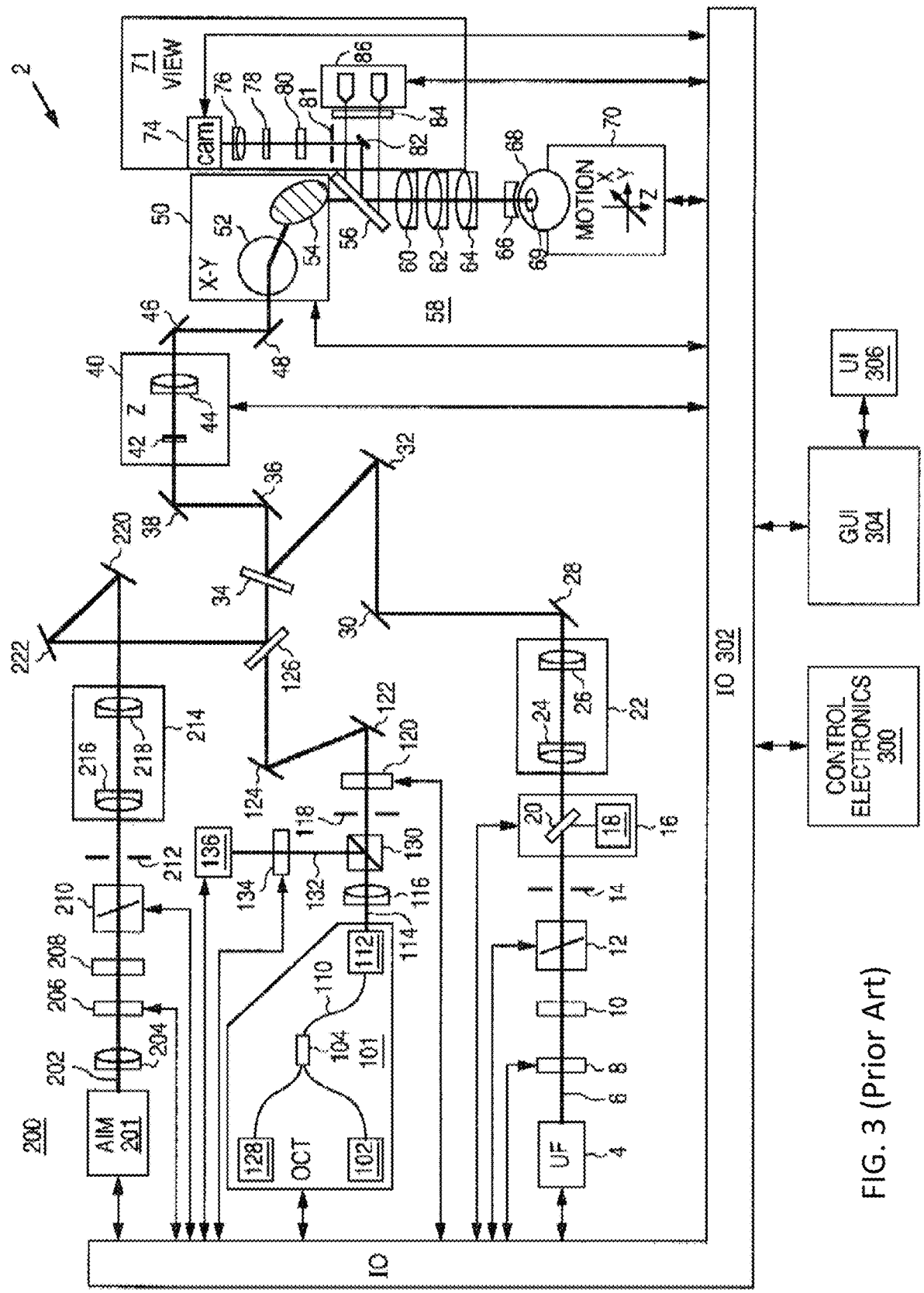
FIG. 3 is a schematic diagram of the optical beam scanning system with an alternative OCT configuration.

Another alternate embodiment is shown in FIG. 3 which is similar to that of FIG. 1 but utilizes an alternate approach to OCT 100. In FIG. 3, OCT 101 is the same as OCT 100 in FIG. 1, except that the reference arm 106 has been replaced by reference arm 132. This free-space OCT reference arm 132 is realized by including beamsplitter 130 after lens 116. The reference beam 132 then proceeds through polarization controlling element 134 and then onto the reference return module 136. The reference return module 136 contains the appropriate dispersion and path length adjusting and compensating elements and generates an appropriate reference signal for interference with the sample signal. The sample arm of OCT 101 now originates subsequent to beamsplitter 130. The potential advantages of this free space configuration include separate polarization control and maintenance of the reference and sample arms. The fiber based beam splitter 104 of OCT 101 can also be replaced by a fiber based circulator. Alternately, both OCT detector 128 and beamsplitter 130 might be moved together as opposed to reference arm 136.

Figure 4:
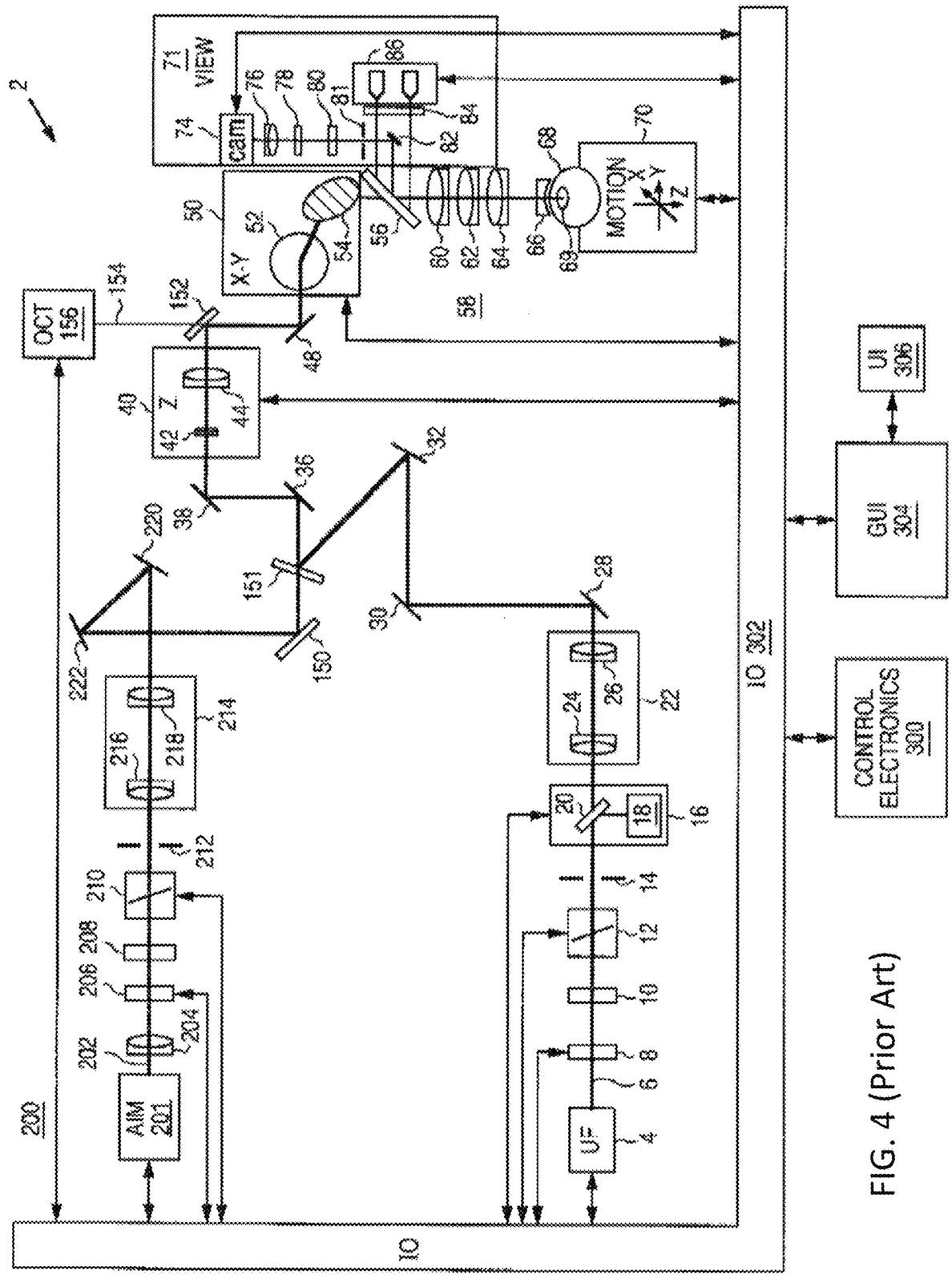
FIG. 4 is a schematic diagram of the optical beam scanning system with another alternative OCT combining scheme.

FIG. 4 shows another alternative embodiment for combining OCT beam 114 and UF beam 6. In FIG. 4, OCT 156 (which can include either of the configurations of OCT 100 or 101) is configured such that its OCT beam 154 is coupled to UF beam 6 after the z-scan 40 using beamcombiner 152. In this way, OCT beam 154 avoids using the z-adjust. This allows the OCT 156 to possibly be folded into the beam more easily and shortening the path length for more stable operation. This OCT configuration is at the expense of an optimized signal return strength as discussed with respect to FIG. 1. There are many possibilities for the configuration of the OCT interferometer, including time and frequency domain approaches, single and dual beam methods, swept source, etc., as described in U.S. Pat. Nos. 5,748,898; 5,748,352; 5,459,570; 6,111,645; and 6,053,613 (which are incorporated herein by reference.)

The device according to FIGS. 1-4 is suitable for scanning 3-dimensional patterns within lens 69 and cornea of the patient's eye 68 as described in U.S. Pat. No. 9,278,028, the entirety of which is incorporated by reference in its entirety. Suitable patterns may be scanned using the laser to provide convenient splitting of lens 69 into segments that are easy to aspirate using existing technology and devices. Phacoemulsification is particularly well suited for this. Several such aspiration devices are commercially available and well known in the art.

Full Depth Laser Ophthalmic Surgical System using a Focal Point Extension Assembly. A first aspect of the present invention is directed to a Full Depth Laser Ophthalmic Surgical System. Most prior ophthalmic surgical systems are capable of only being used for a portion of the eye. These include the system described in detail later with reference to FIGS. 1-4 (referred to hereinafter as "the existing laser ophthalmic surgical system"), which, when used with a corresponding patient interface device having a lens with a predefined optical power, can focus the laser beam in the region of the eye from the cornea to about the location of the lens posterior in the patient. Traditionally, other surgical systems, or cold steel methods, would be required for surgical interventions on the eye that were posterior to the lens, such as surgical interventions in the vitreous humor or the retina. According to an embodiment of the present invention, a removeable lens assembly has been made which extend the focal point of the existing laser ophthalmic surgical system so that the focal point of the laser system can be extended to portions of the eye posterior to the lens. This "focal point extension assembly" extends the focal point of the existing laser ophthalmic surgical system so that it can reach the vitreous humor and the retina. Thus, the existing laser ophthalmic surgical system coupled with the removeable focal point extension assembly create a "full depth" ophthalmic surgical system capable of performing surgical procedures along the entire length of the eye.

Figure 5A:
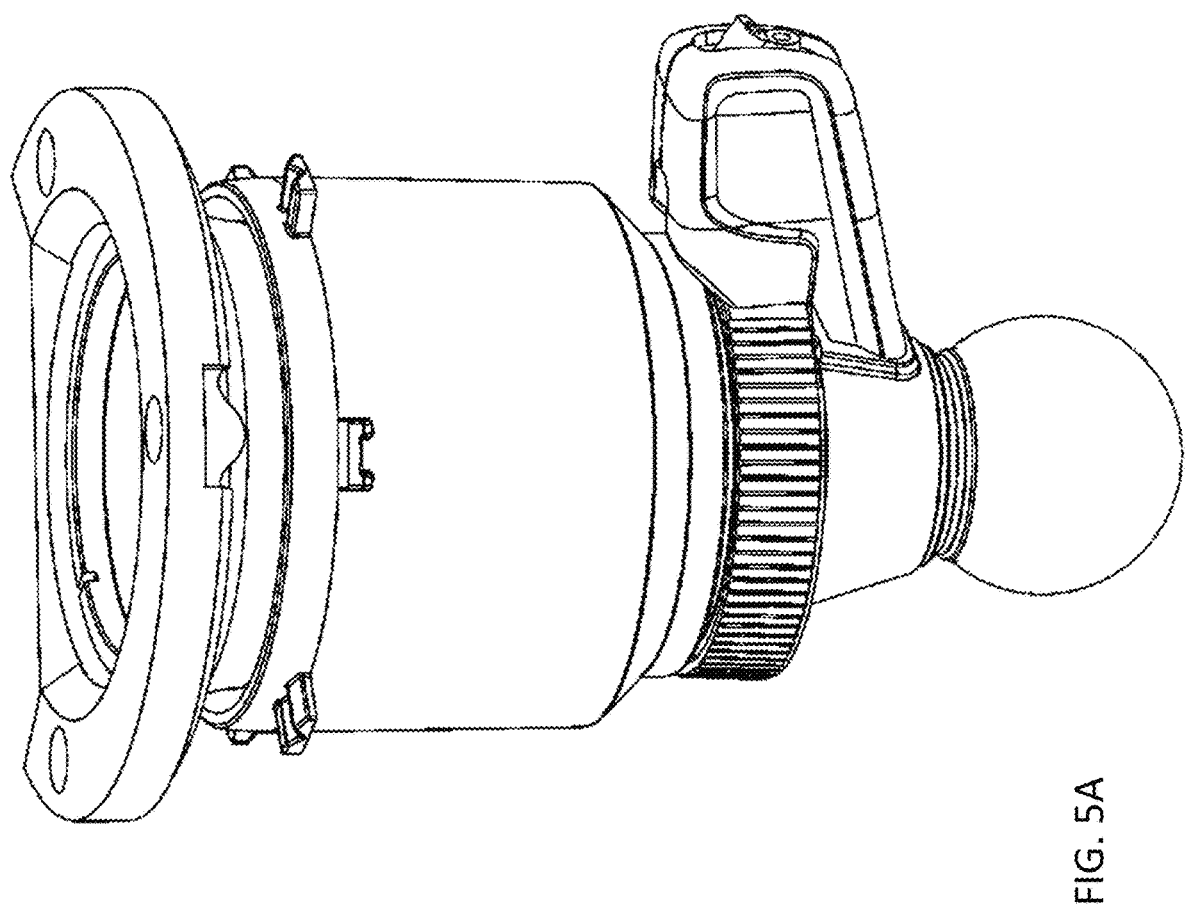
FIG. 5A is a frontal view of a removable focal zone extension adapter configured to extend the focal zone of the optical beam scanning system of FIGS. 1-4 so that the focal zone can extend into the portions of the eye posterior to the lens capsule.
Figure 5B:
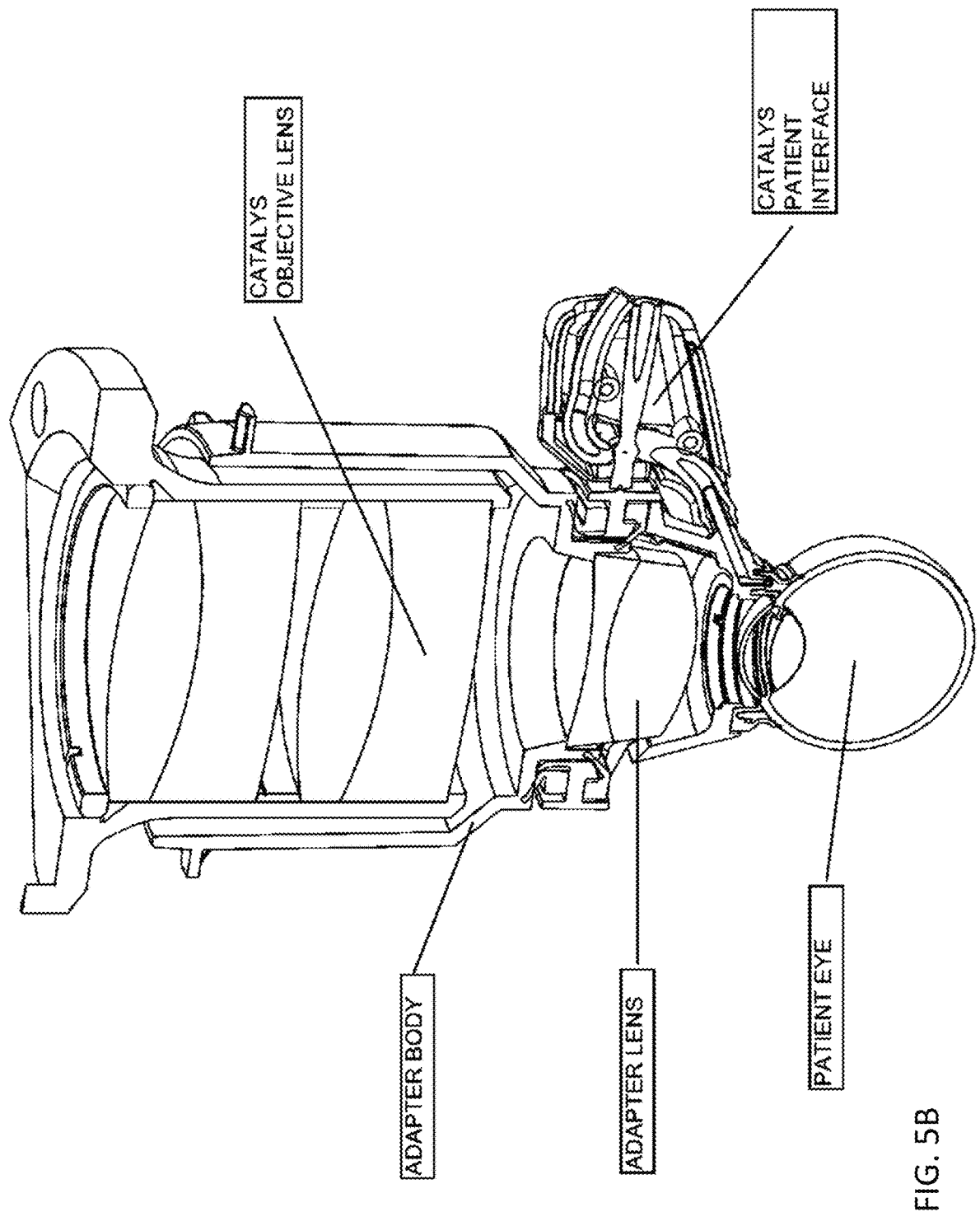
FIG. 5B is a sectional view of the focal zone adapter of FIG. 5A.

FIGS. 5A and 5B illustrate an example of a modified patient interface that incorporates a focal point extension assembly, which is configured to extend the focal zone of the existing laser ophthalmic surgical system so that the focal zone can extend into the portions of the eye posterior to the lens capsule. The modified patient interface constitutes a removable focal zone extension adapter. The patient interface has a structure otherwise similar to an existing patient interface, such as that described in U.S. Pat. Appl. Pub. No. 2013/0102922, published Apr. 25, 2013 (the content of which is incorporated herein by reference in its entirety), but includes an optical assembly (an adapter lens) that provides a less positive or more negative optical power (as compared to the patient interface that is used with the same existing laser ophthalmic surgical system when treating the lens of the eye) to lengthen the focus. In the embodiment shown in FIG. 5B, the optical assembly is a doublet, i.e. two lenses joined together, without any air gap in between. This optical element provides better optical property and correspondingly better beam quality than a single lens. In addition, the optical assembly is optimized to achieve a reasonable beam quality over a reasonable field such as substantially the entire distance between the retina and the posterior lens capsule. In the embodiment shown in FIG. 5B, the upper end of the modified patient interface is configured to be attached to the objective lens assembly of the laser beam delivery system, and the lower end of the patient interface has a suction ring configured to engage the patient's eye via a vacuum force. The structures of the upper and lower ends of the patient interface are similar to those in the above-cited patent.

Note that the modified patient interface having the focal point extension assembly extends the focus distances of both the treatment laser and the imaging system beam, as well as that of the aim beam. A calibration or registration procedure as a function of X, Y Z should be conducted using the modified patient interface in order to match the OCT signal information to the treatment later focus location and also to the relate to absolute dimensional quantities. As described earlier, a calibration or registration procedure is conducted for the existing patient interface. The resulting calibration parameters for both calibrations, for example, in the form of different lookup tables, are stored in the controller.

Thus, when using the existing laser ophthalmic surgical system to perform surgical procedures in the vitreous humor of the eye, the modified patient interface having the focal point extension optical assembly is used, along with the corresponding calibration parameters; when using the same existing laser ophthalmic surgical system to perform surgical procedures in the anterior portions of the eye such as the cornea, the lens capsule and the lens, such as for cataract surgery, the existing patient interface without the focal point extension optical assembly is used, along with the corresponding calibration parameters. This allows the same laser system to be used to treat the full range of locations of the eye.

Figure 6:
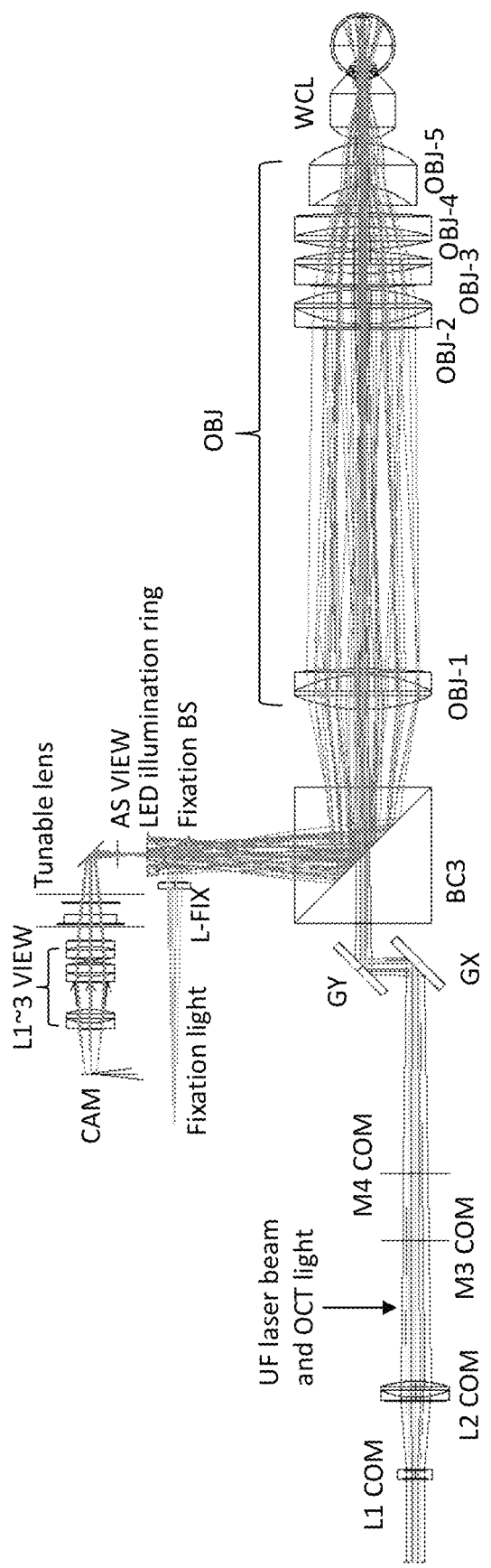
FIG. 6 schematically illustrates an exemplary optical system that can scan the laser beam and the imaging beam within the full range of the eye from the cornea to the retina.

Full Depth Laser Ophthalmic Surgical System optimized for treating the vitreous. In an alternative embodiment of this aspect of the invention, the optical system is configured to scan the laser beam and the imaging beam (e.g., the OCT light) in the Z (depth) direction within the full range of the eye, from the cornea to the retina; the optical parameters (such as the NA and the Strehl ratio) are optimized for scanning the laser beam and the imaging beam in the entire vitreous volume. FIG. 6 schematically illustrates an example of such an optical system. As shown in FIG. 6, the laser beam and the imaging beam, having been directed into the same optical path by a beam combiner (not shown in FIG. 6), passes through a Z-scanner, which includes a lens L1 COM that is moveable along the optical axis. In a preferred embodiment, the lens L1 COM is a negative spherical lens having an effective focal length (EFL) of −39.90 mm and a back focal length (BFL) of −40.98 mm (for 632.8 nm light). The laser beam and the imaging beam then pass through another lens L2 COM, and are aligned by two folding mirrors M3 COM and M4 COM and delivered to the XY-scanner which comprises two scanning mirrors GX and GY. The laser beam and imaging beam output from the XY-scanner are transmitted through a beam splitter BC3, and then focused by an objective lens OBJ. The reflected OCT light from the eye travels in the opposite direction through the objective lens OBJ, the beam splitter BC3, and the scanner back to the OCT assembly for detection.

In a preferred embodiment, the objective lens OBJ is a lens group including five lenses OBJ-1 to OBJ-5, with lenses OBJ-1 to OBJ-4 being doublet lenses and the downstream-most lens OBJ-5 being a meniscus lens. Each of OBJ-1 and OBJ-2 has a focal length of 100 mm and each of OBJ-3 and OBJ-4 has a focal length of 150 mm, and the meniscus lens OBJ-5 has an EFL of 616.97 mm and a BFL of 744.43 mm (for 632.8 nm light).

The optical system is intended to be used with patient interface coupled to the downstream end of the objective lens group OBJ during ophthalmic procedures. The patient interface includes a focusing lens WCL. In a preferred embodiment, the focusing lens is plano-convex having a spherical surface at the proximate end (closer to the objective lens) and a flat surface at the distal end (closer to the eye), with an EFL of 30.06 mm and a BFL of 24.87 mm (for 632.8 nm light). The parameters of the meniscus lens OBJ-5 described in the preceding paragraph are optimized for a patient interface having the plano-convex focusing lens WCL described above. In an alternative embodiment, the focusing lens WCL of the patient interface is a double convex lens, and has a convex surface at the distal end. The convex surface facing the eye can help reduce bubbles in the fluid between the focusing lens WCL and the surface of the eye. In such an embodiment, the parameters of the meniscus lens OBJ-5 will be modified accordingly to optimize it for the double convex lens WCL. The doublet lenses and the meniscus lens of the objective lens group OBJ, together with the lens WCL of the patient interface, deliver the focal spots of the laser beam and the imaging beam to the vitreous volume with minimal aberrations.

The optical system is also configured to direct a fixation light and an illumination light to the eye and direct light reflected or otherwise emitted from the eye back to a video camera for imaging. The fixation light from a fixation light source is collimated by a lens L-FIX, then reflected by a beam splitter Fixation BS to the beam splitter BC3, which in turn reflects the fixation light to the objective lens OBJ. The illumination light, emitted by an LED illumination ring, is transmitted through the beam splitter Fixation BS and then reflected by the beam splitter BC3 to the objective lens OBJ. The objective lens OBJ focuses the fixation light and the illumination light into the eye. An important feature of the camera illumination light source placement and configuration is that it can be pupil matched to the pupil of the patient's eye in a manner similar to locating the image of the X & Y scan mirrors near the pupil (described later). That is, the objective lens group OBJ and the focusing lens of WCL of the patient interface preferably form an image of the illumination source ear the pupil of the patient's eye, and substantially centered with the fixation light, as are images of the X & Y scan mirrors. This configuration allows for illumination of a larger field in the full depth range of the eye. The light reflected or otherwise emitted from the eye travels backwards through the objective lens OBJ and is reflected by the beam splitter BC3. After transmitting through the beam splitter Fixation BS, the light from the eye passes through an aperture AS VIEW and is focused by additional lenses, including a tunable lens and three doublet lenses L1 VIEW to L3 VIEW in a preferred embodiment, onto the camera detector CAM which generates an image of the eye. The tunable lens can be either tunable by moving the lens, or by adjusting the optical power of the lens.

The Z scanner (L1 COM), the XY scanner (GX and GY), and the tunable lens for the video camera CAM are electrically coupled to the controller of the laser ophthalmic surgical system, and controlled by the controller to scan of the laser beam and the imaging beam (e.g. the OCT beam) within the eye and to image the eye with the video camera.

Figure 7:
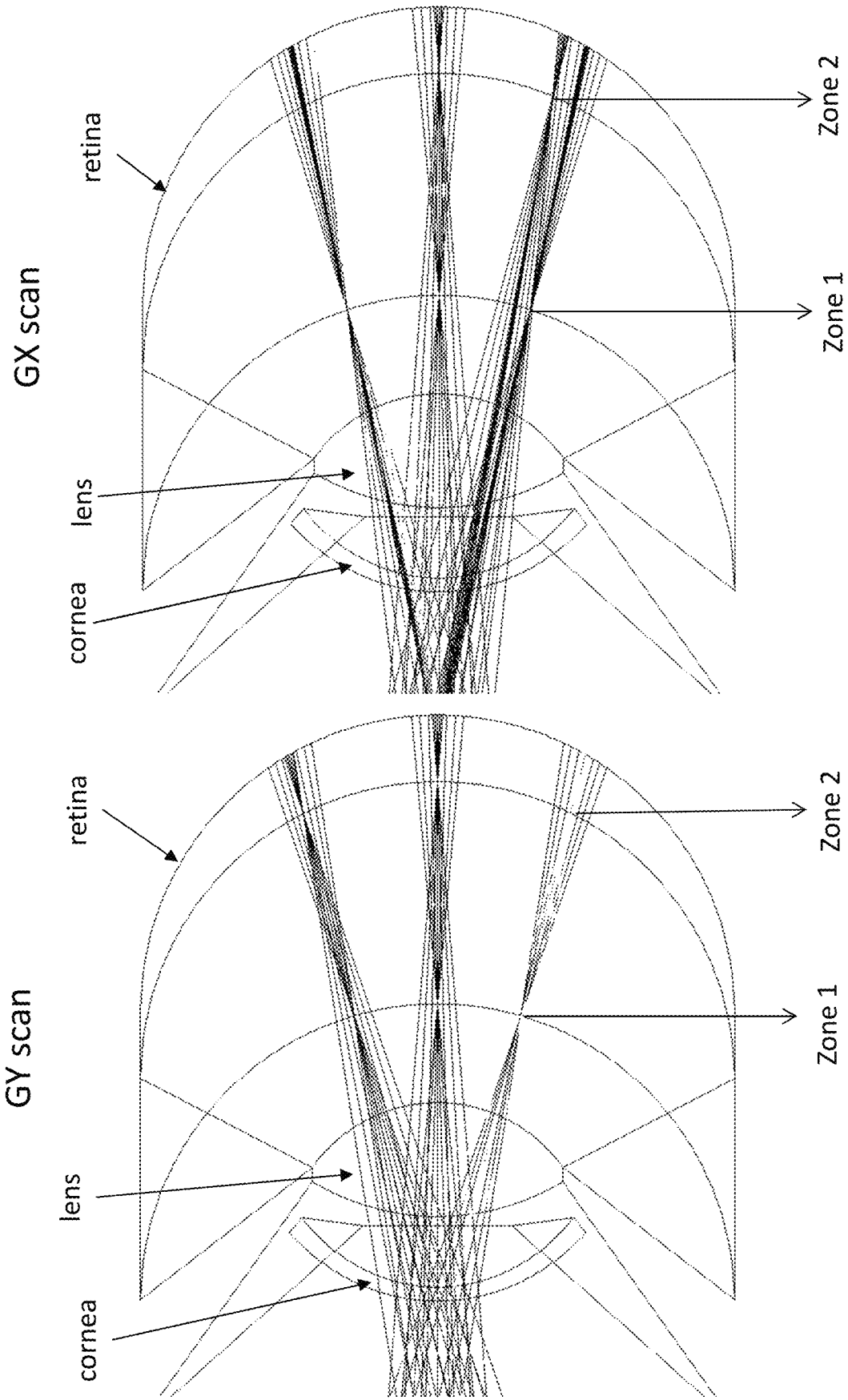
FIG. 7 schematically illustrates the laser light being focused in the vitreous humor of the eye using the optical system of FIG. 6.
Figure 8:
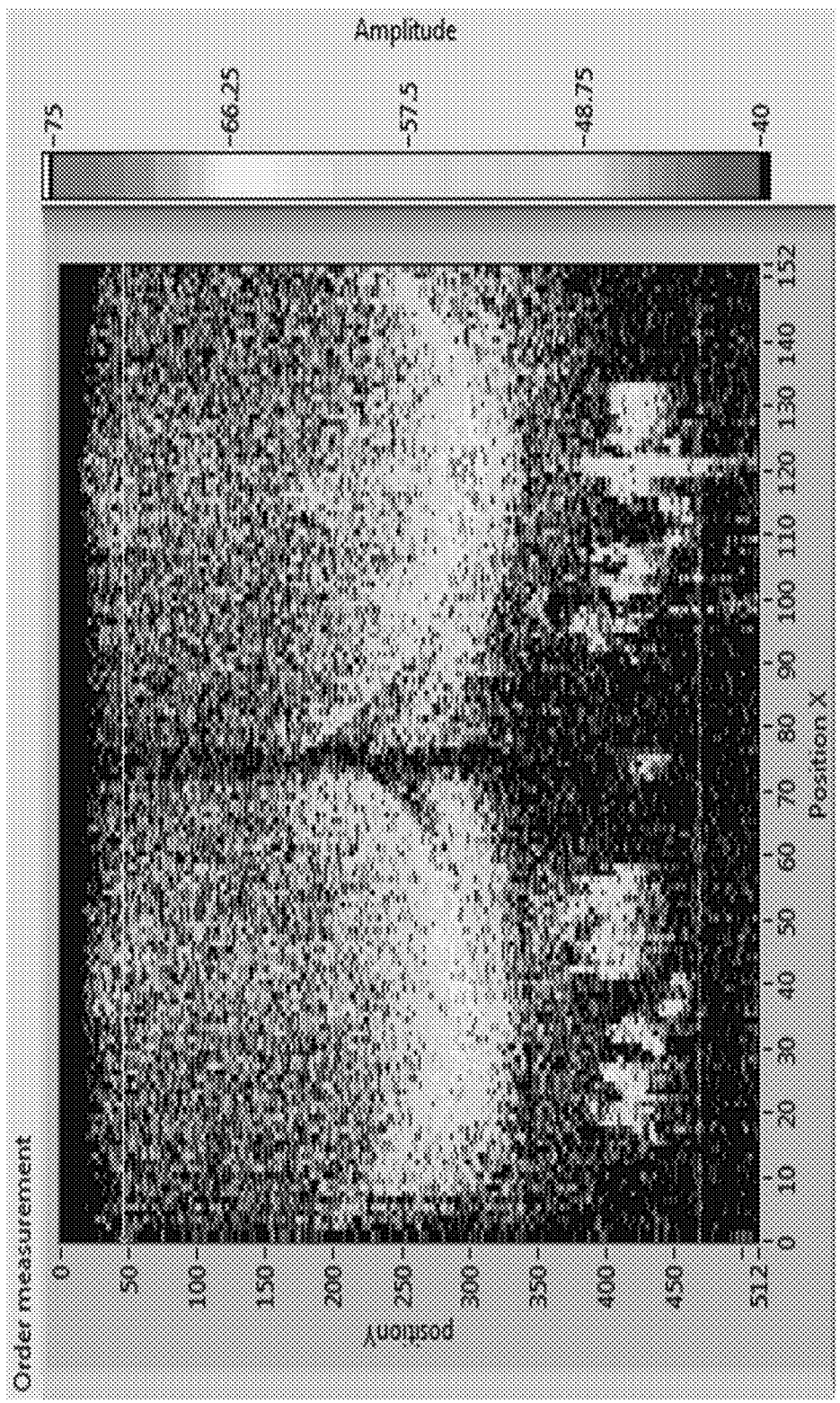
FIG. 8 is an image of the structures of the posterior portion of the eye using the OCT beam.

This optical system is optimized to focus and scan the laser beam and the imaging beam in substantially the entire depth of vitreous humor of the eye from the posterior lens capsule to the retina. In actual surgery, it is desired to maintain safe zones (i.e. zones free of laser focal spot scanning) of a depth of about 4 mm after the lens (the posterior lens capsule) and a depth of about 3 mm before the retina. FIG. 7 schematically illustrates the focusing of the laser beam and the imaging beam in a depth range between the two safe zones, with a viewing angle of 45 degrees for the X scan and 38 degrees for the Y scan. It should be noted that the light exiting the focusing lens WCL of the patient interface is further refracted by the optical elements of the eye, including the cornea and the lens of the eye (it should be noted, however, that due to the fluid bath in the patient interface that contacts the cornea, focusing by the cornea tends to be minimal); the optical system design takes this into consideration. Moreover, when the patient interface is one where the distal surface of the focusing lens WCL does not directly contact the cornea of the eye but uses a fluid bath located between the WCL lens and the cornea, the relative distance of the patient's eye from the WCL lens surface is a function of the design of the patient interface such as the size of the fluid chamber. Thus, the optical system is designed such that the focusing range covers the entire desirable range within the eye after taking into consideration all of the factors discussed above. In one particular example, the optical system is designed such that without the eye, the focal spot of the laser beam can be scanned within a depth range of 15 mm to 24 mm in water beyond the distal surface of the focusing lens WCL of the patient interface.

As shown in FIG. 7, the optical system focuses the laser beam and imaging beam within the vitreous volume with wide viewing angles in both the X and Y scanning directions. This is achieved by the objective lens group OBJ and the focusing lens of WCL of the patient interface, which together function as relay optics to form respective images of the scanning mirrors GX and GY at locations near or at the pupil plane of the eye, as shown in FIG. 7C. In a conventional optical beam scanning system that is designed to scan the focal spot of the laser to treat the anterior segments of the eye including the cornea and the lens, as illustrated in FIG. 7A, the depth range of the focal spot is typically limited to the lens posterior capsule. When the conventional optical beam scanning system is used with a different patient interface lens that extends the depth range of the laser focal spot to the vitreous and the retina, as shown in FIG. 7B, due to the fact that in such conventional optical beam scanning system the pivot points of the scanning mirrors GX and GY are located far away from the pupil of the eye, the pupil diameter limits the transverse scanning range of the beam. In this situation, the volume that can be reached by the laser focal spot is approximately a tapered cylinder that has a maximum diameter less than the pupil diameter. In embodiments of the present invention, as shown in FIG. 7C, due to the relay optics, the scanned laser beam emanates from the locations of the images of the scanning mirrors GX and GY, which are located near or at the pupil plane of the eye. This makes the scanning angle in the eye much wider, and the beam can reach a volume in the vitreous that has a maximum diameter larger than the pupil diameter. In a preferred embodiment, the images of the scanner mirrors are located about 0 to 5 mm from the patient's iris plane. When the system is used with a patient interface that employs a fluid bath between the cornea and the distal surface of the focusing lens WCL of the patient interface, the optical design takes into account the approximate distance between the WCL lens surface and the cornea in order to form the images of the scanner mirrors at the above-described desired location relative to the patient's iris plane. In one particular example, the optical system is designed such that the images of the scanner mirrors are located about 0 to 10 mm from the distal surface of the focusing lens WCL of the patient interface. It should be noted that the same considerations apply to the design of the optical system to form an image of the illumination light source near the iris plane as discussed earlier. In operation, the depth location of the iris from the distal surface of the focusing lens of the patient interface may be measured, and the objective lens is controlled to form the image of the scanning mirrors, as well as the illumination light as mentioned earlier, at the pupil.

By using the tunable lens before the video camera, the optical system is configured to focus light emitted anywhere within the entire depth of the eye onto the video camera CAM, so as to image different planes of the eye from the iris to the retina. Again, the light emitted from the vitreous of the eye will be refracted by optical elements of the eye such as the lens (and to a much lesser extent the cornea), and the design of the optical system takes this into consideration. Without the eye, the optical system can image objects within a depth range of 8 mm to 29 mm in water beyond the distal surface of the focusing lens WCL of the patient interface. In a preferred embodiment, the tunable lens has a tunable range of −10D to +10D. As mentioned earlier, the tunable lens can be either tunable by adjusting the optical power of the lens, or by moving an imaging lens having a fixed optical power. Such a fixed power lens may be mounted on a mechanically moveable stage (moved by a motor or an actuator), and the movement of the stage is controlled by the controller to change the imaging location of the video camera. The movement range of the stage is configured to allow the video camera to image different planes of the eye from the iris to the retina.

The illumination light source is ring shaped, and located near the aperture AS VIEW of the video camera and coaxially with the optical axis of the video camera. This configuration allows the illumination light to illuminate a wide field and the entire depth range from the iris to the retina to aid camera imaging.

While the optical system of this alternative embodiment is described in considerable detail, variations of the optical design are also within the scope of the invention, so long as they can scan the laser beam and the imaging beam to the desired depth range within the eye, direct the illumination light to a wide field and the entire depth range of the eye, and focus the light emitted from the entire depth range eye to the video camera. For example, different combinations of imaging lenses to reach the same or different F numbers or magnifications may be used.

Systems and methods for calibrating the Ophthalmic Surgical Systems for procedures performed posterior to the lens. A problem associated with using laser systems, such as that according to FIGS. 1-4 in the posterior portion of the eye is that it is very difficult to properly calibrate the surgical system for use in the posterior portion. This is due to the fact that there is an unknown optical element, i.e. the patient's lens (with an unknown refractive power), between the laser source and location of the focal zone in the patient's eye. As a result of this unknown optical element, there can be a significant difference between the apparent location of the focal zone and the actual location of the focal zone. This can be dangerous as the focal zone could unknowingly be in dangerous location. While using average values for eye physiology may be satisfactory for much of the population, there could be a significant risk for persons whose eyes are outside normal physiological averages. One method is to use structural data of the lens of the patient's eye, obtained using the OCT system, to determine the individual active optical power of the lens, in order to accurately place the laser focus within the vitreous volume. Alternatively, fast and efficient calibration methods can be done for each individual patient as described below.

One aspect of the present invention is directed to systems and methods for calibration of laser surgical systems for use in portions of the eye that are posterior to the human lens. A system and method for the calibration is based on the use of the imaging subsystem's optical coherence tomographer. In essence, the focal zone of the optical coherence tomographer beam is used as a proxy for the focal zone of the femtosecond laser source. This method may be implemented using either the existing laser ophthalmic surgical system with the modified patient interface shown in FIG. 5B, or a laser ophthalmic surgical system having the optical system shown in FIG. 6.

The method can be summarized by the following steps:
1. Use the OCT to find the relevant structure (i.e. the retina) based on an area of bright return of the OCT beam;
2. Move the focal zone of the OCT beam in the anterior direction by a predetermined distance from the relevant structure identified in step 1 (the predetermined distance corresponds to a safety zone, e.g. 2 mm from the retina);
3. Set this new location as the safe limiting position of the focal zone of the laser beam;
4. Repeat for other relevant structures as necessary (i.e. posterior portion of the lens capsule, in which case the safety limitation position is a predetermined distance (e.g. 2 mm) in the posterior direction of the lens posterior capsule)

More specifically, the focal zone of OCT beam is scanned in the depth direction (using the Z scan device of the laser system) in regions of the eye posterior to the posterior lens capsule, and the intensity of the returned (i.e. reflected) OCT beam is measured as a function of depth. Peaks of the intensity function are identified to determine the depth location of the retina, the posterior lens capsule, and optionally other structures of the eye. The safety limiting depths are set based on the depths of the retina and posterior lens capsule, e.g., at 2 mm anterior of the retina and 2 mm posterior of the posterior lens capsule. Note that this safety distance is a function of pulse energy. Other appropriate safety values may be determined based on experiments. The parameters of the Z scan device that correspond to these various depths are determined, which can then be used by the controller to scan the focal zone of the treatment laser beam for treating the vitreous humor, e.g. to treat floaters or liquefy the vitreous humor as described herein. The scan of the treatment beam is performed within the volume bound by the safety limitation positions described above. This method allows one to safely set the location of the laser beam taking into account the individual refractive power of each person's eye and at the same time allows one to identify a safe surgical zone for the ophthalmic surgery in portions of the eye posterior to the lens.

Treatment Methods and Systems Carrying out the Method: Liquification of the Vitreous Humor. Surgical procedures sometimes require removal of the vitreous. However, this can be difficult because of the gelatin like structure of the vitreous. In addition, the vitreous may be adhered to various delicate structures of the eye (e.g. the retina) and it can be difficult to remove the vitreous without disturbing other structures. An in vitro study in rabbits performed by the instant inventors showed the liquification of the vitreous humor with the femtosecond laser surgical system described above can be performed safely. Liquification of the vitreous may be indicated in surgical procedures where removal of the vitreous is required.

To liquefy the vitreous humor, either the existing laser ophthalmic surgical system with the modified patient interface shown in FIG. 5B, or a laser ophthalmic surgical system having the optical system shown in FIG. 6, is used. The retina and the lens posterior capsule are located, for example using the process described above. The imaging system such as the OCT system may be used to image the structure of the vitreous humor to identify the outer boundaries for liquification. The outer boundaries may be determined by the human operator or by the controller based on the images. A treatment plan can then be defined with the assistance of the controller. For example, a scan pattern of the laser focal spot within the volume defined by the boundaries can be programmed using the controller. The treatment plan is then executed to scan the focal spot of the laser beam according to the scan pattern, to thereby perform a volumetric treatment of the vitreous humor to enable liquification. The following laser beam parameters may be used in preferred embodiments: Wavelength: preferably 1000-1100 nm, and more preferably 1030 nm; pulse width: preferably 100-1000 fs, and more preferably 100-600 fs; pulse energy: preferably 2-20 µJ; repetition rate: preferably 1-500 kHz; total energy: preferably less than 40 J. In an animal test using rabbit eyes, the following laser parameters were used to successfully liquefy the vitreous humor: Wavelength: 1030 nm; pulse width: about 400 fs; pulse energy: about 9 µJ; repetition rate: 6-24 kHz; total energy: 10-40 J.

Treatment Methods and Systems Carrying out the Method: Treatment of floaters and other vitreous treatment. In addition to vitreous liquification, either the existing laser ophthalmic surgical system with the modified patient interface shown in FIG. 5B, or a laser ophthalmic surgical system having the optical system shown in FIG. 6, may be used to treat vitreous floaters. The OCT and/or the video camera system may be used to locate the vitreous floaters, and treatment plan is determined and executed to specifically target the floaters for treatment. For example, the laser focal spot may be scanned in a volume that includes the floaters to destroy or remove the floaters. Further, the system may be used to pre-treat the vitreous volume before vitrectomy to simplify the surgical procedure and reduce possible complications.

In this disclosure, as is customary in the field of ophthalmic surgery, the term "depth" refers to a direction of the eye that extends from cornea to the retina; it corresponds to the Z direction of the laser ophthalmic surgical system as described above. The terms "anterior" and "posterior" are relative terms and refer to locations closer to the cornea and closer to the retina, respectively.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

While certain illustrated embodiments of this disclosure have been shown and described in an exemplary form with a certain degree of particularity, those skilled in the art will understand that the embodiments are provided by way of example only, and that various variations can be made without departing from the spirit or scope of the invention. Thus, it is intended that this disclosure cover all modifications, alternative constructions, changes, substitutions, variations, as well as the combinations and arrangements of parts, structures, and steps that come within the spirit and scope of the invention as generally expressed by the following claims and their equivalents.

The invention claimed is:

1. A full depth ophthalmic surgical system for performing surgery on an eye of a subject, comprising:
    a femtosecond laser source configured to produce a femtosecond pulsed laser beam;
    an imaging assembly configured to emit an imaging beam;
    a scanning assembly including a Z scanner and an XY scanner, configured to scan a focal spot of the laser beam and the imaging beam within the eye in a depth direction and two transverse directions, respectively;
    an illumination light source configured to emit an illumination light;
    a video camera assembly, including a detector and a tunable lens in front of the detector;
    an objective lens assembly configured to focus the laser beam and the imaging beam;
    a patient interface configured to be coupled to the objective lens assembly and to engage the eye, the patient interface including a lens having a predefined optical power; and
    optical components including at least one beam splitter, configured to direct the laser beam and the imaging beam output by the scanning assembly and the illumination light to the objective lens assembly, and to direct light emitted from within the eye, which has passed through the objective lens assembly, to the video camera assembly;
    wherein the scanning assembly, the objective lens assembly and the lens of the patient interface are configured to form the focal spot of the laser beam at any and all depths within a range of 15 mm to 24 mm in water beyond a distal surface of the lens of the patient interface, and
    wherein the tunable lens is configured to cooperate with the objective lens assembly and the lens of the patient interface to focus light emitted from any and all distances within a range of 8 mm to 29 mm in water beyond the distal surface of the lens of the patient interface onto the detector to produce images of any and all tissues of the eye from an iris to a retina, including regions of a vitreous humor, on the detector.

2. The ophthalmic surgical system of claim 1, wherein the illumination light source is a ring-shaped light source.

3. The ophthalmic surgical system of claim 2, wherein the objective lens assembly and the lens of the patient interface are configured to form an image of the illumination light source at locations 0 to 10 mm from a distal surface of the lens of the patient interface.

4. The ophthalmic surgical system of claim 1, wherein the objective lens assembly includes four doublet lenses and a meniscus lens.

5. The ophthalmic surgical system of claim 1, wherein the imaging assembly comprises an optical coherence tomographer, a Purkinje imaging assembly, or a Scheimpflug imaging assembly.

6. The ophthalmic surgical system of claim 1, further comprising a fixation light source configured to generate a fixation light, wherein the optical components are further configured to direct the fixation light to the objective lens assembly.

7. The ophthalmic surgical system of claim 1, wherein the XY scanner includes two scanning mirrors, and wherein the objective lens assembly and the lens of the patient interface are configured to form respective images of the two scanning mirrors at locations 0 to 10 mm from a distal surface of the focusing lens of the patient interface.

8. The ophthalmic surgical system of claim 1, further comprising a controller operably connected to the laser source, the imaging assembly, the scanning assembly, and the video camera assembly and programmed to:
   operate the imaging assembly to form images of structures within a vitreous humor of the eye;
   identify outer boundaries of a treatment volume located in the vitreous humor based on the images;
   define a scan pattern for scanning the focal spot of the laser beam within the treatment volume; and
   operate the scanning assembly to scan the focal spot of the laser beam in the treatment volume in the vitreous humor according to the scan pattern to liquify the vitreous humor in the treatment volume.

9. The ophthalmic surgical system of claim 1, further comprising a controller operably connected to the laser source, the imaging assembly, the scanning assembly, and the video camera assembly and programmed to:
   operate the imaging assembly or the video camera assembly to form images of structures in a vitreous humor of the eye;
   identify floaters located in the vitreous humor based on the images;
   define a treatment volume within the vitreous humor that includes the identified floaters;
   define a scan pattern for scanning the focal spot of the laser beam within the treatment volume; and
   operate the scanning assembly to scan the focal spot of the laser beam in the treatment volume in the vitreous humor according to the scan pattern to destroy or remove the floaters.

10. The ophthalmic surgical system of claim 1, wherein the tunable lens has a tunable range of −10D to +10D.

11. The ophthalmic surgical system of claim 1, further comprising a programmed controller operably connected to and controlling the tunable lens of the video camera assembly.

* * * * *